United States Patent [19]

Cramm et al.

[11] Patent Number: 5,283,338
[45] Date of Patent: Feb. 1, 1994

[54] PROCESS FOR THE PREPARATION OF 2-CHLOROPYRIDINES

[75] Inventors: Günther Cramm; Hans Lindel, both of Leverkusen; Guido Steffan, Odenthal, all of Fed. Rep. of Germany

[73] Assignee: Bayer Aktiengesellschaft, Leverkusen, Fed. Rep. of Germany

[21] Appl. No.: 861,039

[22] Filed: Apr. 1, 1992

[30] Foreign Application Priority Data

Apr. 6, 1991 [DE] Fed. Rep. of Germany ....... 4111215

[51] Int. Cl.$^5$ ................. C07D 213/26; C07D 213/61
[52] U.S. Cl. .................... 546/345; 546/304; 546/346
[58] Field of Search ......................... 546/345

[56] References Cited

U.S. PATENT DOCUMENTS

| | | | |
|---|---|---|---|
| 3,200,040 | 8/1965 | Lange et al. | 8/409 |
| 3,536,436 | 10/1970 | Lange et al. | 8/409 |
| 3,632,807 | 1/1972 | Maurer et al. | 546/345 |
| 4,133,675 | 1/1979 | Schurter et al. | 504/191 |
| 4,348,396 | 9/1982 | Kierstead et al. | 514/267 |
| 4,404,388 | 9/1983 | Fab | 546/345 |
| 4,612,377 | 9/1986 | Osborne et al. | 546/345 |
| 4,678,795 | 7/1987 | Shiokawa et al. | 514/341 |
| 4,831,148 | 5/1989 | Schurter et al. | 546/345 |
| 5,010,201 | 4/1991 | Kaufmann et al. | 546/316 |

FOREIGN PATENT DOCUMENTS

| | | | |
|---|---|---|---|
| 0178260 | 4/1986 | European Pat. Off. | 546/345 |
| 1178052 | 9/1964 | Fed. Rep. of Germany | 544/217 |
| 1695659 | 12/1971 | Fed. Rep. of Germany | 546/345 |
| 0870027 | 8/1959 | United Kingdom | 534/574 |

OTHER PUBLICATIONS

The Merck Index, Eleventh Edition, p. 756 pub. by Merck and Co., Inc. (1989).

P.A.S. Smith, The Chemistry of Open-drain Organic Nitrogen Compounds, vol. II, Benjamin Pubs. (1966).
Leland J. Beckham, et al., "Nitrosyl Chloride", Chem. Rev. 48 (1951), pp. 319, 341 and 393.
H. Albers et al, "Heterocyclic compounds", Chem. Abstracts, V. 61, pp. 16079–16080 Dec. 1964.
Charles L. Bell, "Nuclear Magnetic Resonance Studies of Heteroaromatic Systems. Methyl Coupling of 2-Substituted Picolines, 2-Pyridones and 2-Pyridthiones," (1965), pp. 420–429.

*Primary Examiner*—Alan L. Rotman
*Attorney, Agent, or Firm*—Sprung Horn Kramer & Woods

[57] ABSTRACT

2-Chloropyridine derivatives of the formula (I)

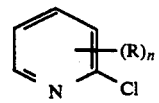

(I)

in which
R represents hydrogen, $C_1$–$C_4$-alkyl or halogen and n represents 0 to 4, are obtained in good yields and high purity when a 2-aminopyridine derivative of the formula (II)

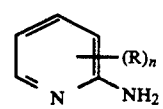

(II)

in which
R and n have the above definitions, is reacted with nitrosyl chloride in a hydrogen chloride-saturated aqueous solution at temperatures between −10° C. and +50° C. with simultaneous introduction of hydrogen chloride.

1 Claim, No Drawings

PROCESS FOR THE PREPARATION OF 2-CHLOROPYRIDINES

It is known that 2-aminopyridines can be converted into the corresponding 2-chloropyridines with the aid of the Sandmeyer reaction or similar reactions. The best yields are obtained on reaction with alkyl nitrites having preferably 3 to 5 carbon atoms in a saturated hydrochloric acid-containing methanolic solution (DE A 16 95 659). A prerequisite for this is a molar ratio of 2-aminopyridine to methanol of 1:8 to 1:12.

It is seen as an important disadvantage of the process according to DE-A 16 95 659 that the formation of methyl chloride cannot be avoided, in particular with an economically justifiable recovery of methanol. A further disadvantage is the use of alkyl nitrites such as butyl, amyl or propyl nitrite, since the alcohols resulting from them can only be separated from the solvent methanol with great difficulty.

It is further known that 2-chloro-pyridines are obtained when alkyl-2-pyridones are reacted in the presence of N,N-disubstituted formamides with phosgene (e.g. EP-A 72 777), or 5,6-dihalogeno-2-piperidinone is treated with POCl$_3$ or phosgene and subsequently with bases (e.g. EP-A 121 320), or pyridine-N-oxides are reacted with chlorine-containing phosphoric acid derivatives (e.g. DE-A 3 839 332).

It is further known that 2-chloropyridines are obtained when 2-amino-pyridines are reacted with sodium nitrite in aqueous hydrochloric acid-containing solution (e.g. J. Heterocycl. Chem. 2, 1965, 420).

The diazotisation in aqueous hydrochloric acid gives yields of only 30 to at most 50% of 2-chloropyridines; the main products are the corresponding hydroxyl compounds.

It has now been found that 2-chloropyridine derivatives of the formula (I)

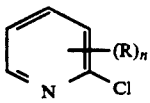

in which
R represents hydrogen, C$_1$–C$_4$-alkyl or halogen and
n represents 0 to 4,
are obtained in good yields and high purity when a 2-aminopyridine derivative of the formula (II)

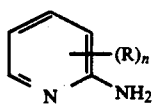

in which
R and n have the above definitions,
is reacted with nitrosyl chloride in a hydrogen chloride-saturated aqueous solution at temperatures between −10° C. and +50° C. with simultaneous introduction of hydrogen chloride.

The reaction according to the invention is preferably used for the preparation of compounds of the formula (I) in which R represents hydrogen, chlorine or C$_1$–C$_2$-alkyl and n is 1 or 2. In particular the compound 2-chloro-5-methyl-pyridine is prepared by the process according to the invention.

Surprisingly, 2-chloropyridine derivatives can be prepared by the process according to the invention by relatively simple means in very good yield and in high purity, whereas known methods give these products in moderate yields and unsatisfactory quality.

Further advantages of the process according to the invention are the use of water as solvent (advantages the recycling and disposal of waste and residues), the complete avoidance of the formation of alkyl chlorides (as are formed during reactions of alkyl nitrites in methanol). moreover, no phosphate-polluted effluents are produced (as in reactions with phosphoric acid derivatives), and the complicated handling of phosgene because of safety precautions is avoided.

When 2-amino-5-methylpyridine, HCl and nitrosyl chloride are used as starting materials, the course of the reaction may be described as follows:

The 2-amino-pyridine derivatives of the formula (II) to be used as starting materials are known. The nitrosyl chloride to be used is also known.

Specific examples of 2-aminopyridines of the formula (II) which can be used in the process according to the invention are:
2-amino-5-methyl-pyridine, 2-amino-3-methyl-pyridine, 2-amino-4-methyl-pyridine, 2-amino-6-methyl-pyridine, 2-amino-pyridine, 2-amino-4-chloro-pyridine, 2-amino-5-ethyl-pyridine, 2-amino-3,5-dimethyl-pyridine. The use of 2-amino-5-methyl-pyridine is especially preferred.

The process according to the invention is carried out by reacting the 2-aminopyridine derivative with nitrosyl chloride in HCl-saturated aqueous solution. During this, hydrogen chloride gas is introduced simultaneously, so that the reaction mixture is always saturated with hydrogen chloride.

1 to 5 molar equivalents, preferably 1.1 to 3 molar equivalents, of nitrosyl chloride are used per mole of aminopyridine starting material.

The process is generally carried out at temperatures between −10° C. and +50° C., preferably between 0° C. and +20° C. Generally, atmospheric pressure is used.

When the reaction is complete, the reaction mixture is concentrated, then rendered alkaline by means of bases (especially by means of alkali metal hydroxide), and the organic phase is separated off. The 2-chloropyridine is obtained in pure form from the organic phase, preferably by distillation.

Alternatively to this, after the mixture has been rendered alkaline, the reaction product can also be isolated by azeotropic distillation with water. The azeotrope thus obtained can be separated from the water and, together with the abovementioned organic phase, subjected to a distillation.

The reaction according to the invention gives a 2-pyridone derivative as a by-product; this is found during work-up in the mother liquor after separating off the organic phase, the 2-pyridone derivative crystallising out on further concentration (distilling off water). After separation of the 2-pyridone derivative, this can be converted into the corresponding 2-chloropyridine derivative by a method known per se, e.g. by the process of German Auslegeschrift (German Published Specification) No. 1 178 052, by reaction with thionyl chloride in the presence of an N,N-dialkyl-substituted formamide. The total yield of 2-chloro-pyridine of the formula (1) can thus be additionally increased.

This work-up of the 2-pyridone-containing mother liquor can be carried out as an additional process measure.

The 2-chloro-5-methyl-pyridine preparable by the process according to the invention is known as an intermediate for pharmaceuticals (cf. DE-A 28 12 585).

Furthermore, 2-chloro-5-methyl-pyridine can be used as an intermediate for the preparation of insecticidal nitromethylene derivatives (cf. EP-A 163 855).

Furthermore, the compounds preparable according to the invention can be used as intermediates for the preparation of diazotype dyes (cf. GB-A 870 027) and hair dyes (cf. DE-A 1 142 045).

Finally, the 2-chloropyridines preparable according to the invention are valuable intermediates for the preparation of herbicidally active α-[4-(pyrid-2-yloxy)-phenoxy]-alkanecarboxylic acids and their derivatives (see in this context Swiss Patent No. 622 170).

Preparation Example

The solution of 540 g of 2-amino-5-methyl-pyridine in 500 g of water or the hydrochloric acid-containing distillate of a previous batch (see below) is saturated at 0° to 10° C. with hydrogen chloride gas. The solution is simultaneously treated with 400 g of nitrosyl chloride and 300 g of hydrogen chloride in gaseous form at 0 to 5° C. After one further hour the majority of the free hydrogen chloride and approximately 500 g of water are distilled off from the reaction solution. The distillate is used again as the reaction medium for the next batch.

The residue is diluted with 500 g of water, or with distillate obtained from the concentration (see below), and adjusted to a pH of 8-9 by means of 7 mol sodium hydroxide at 70°-80° C. The organic phase which separates is removed, and the NaCl-saturated aqueous phase is subsequently concentrated to a quarter of the starting volume.

During this, a small quantity of 2-chloromethylpyridine at first passes over as an azeotrope. It is separated from the water and distilled together with the organic phase over a column. The yield of 2-chloro-5-methyl-pyridine is 535 g, or 83.9% of theory.

The approximately 500 g of water resulting from concentration of the aqueous phase are used to dilute the next batch prior to the neutralisation. The sodium chloride precipitating out after distilling off a further approximately 250 g of water is filtered off hot using suction. The 5-methyl-2-pyridone crystallising out during cooling of the mother liquor is removed, the mother liquor remaining is added to the next batch after the phase separation and the residual pyridone as well is isolated by concentration of the mother liquor as previously described.

The 5-methyl-2-pyridone obtained (87 g, or approximately 16% of theory, relative to the aminomethylpyridine used) is also converted into 2-chloro-5-methylpyridine by a known process (cf. German Auslegeschrift (German Published Specification) 11 78 052).

The total yield of 2-chloro-5-methylpyridine, relative to the aminomethylpyridine used, is 601 g, or 94.1% of theory.

We claim:

1. A process for the preparation of 2-chloro-5-methyl-pyridine of the formula

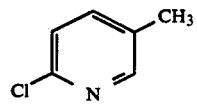

which comprises reacting 2-amino-5-methyl-pyridine of the formula

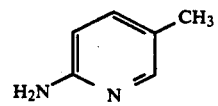

with nitrosyl chloride in a hydrogen chloride saturated aqueous solution at a temperature between 0° C. and 20° C. with simultaneous introduction of gaseous hydrogen chloride.

* * * * *